United States Patent [19]

Fields et al.

[11] 4,309,413

[45] Jan. 5, 1982

[54] METHOD OF PRODUCING IMMUNE RESPONSE BY ADMINISTERING POLYMERIC COMPOSITION

[75] Inventors: Joseph E. Fields, Ballwin, Mo.; Samuel S. Asculai, Rehovot, Israel; John H. Johnson, Kirkwood, Mo.

[73] Assignee: Monsanto Company, St. Louis, Mo.

[21] Appl. No.: 192,663

[22] Filed: Oct. 1, 1980

Related U.S. Application Data

[63] Continuation-in-part of Ser. No. 5,638, Jan. 22, 1979, Pat. No. 4,255,537.

[30] Foreign Application Priority Data

Jan. 18, 1980 [NZ] New Zealand ............... 192649

[51] Int. Cl.³ ............... A61K 31/74; A61K 31/78; A61K 39/00; C08F 8/30
[52] U.S. Cl. ............... 424/78; 424/81; 424/85; 525/328; 525/378
[58] Field of Search ............... 424/78, 81, 85; 525/328, 378

[56] References Cited

U.S. PATENT DOCUMENTS

| | | | |
|---|---|---|---|
| 2,883,287 | 4/1959 | Kosmin et al. | 525/328 |
| 3,157,595 | 11/1964 | Johnson et al. | 210/54 |
| 4,255,537 | 3/1981 | Fields et al. | 525/328 |

FOREIGN PATENT DOCUMENTS

664326 4/1963 Canada .

OTHER PUBLICATIONS

Regelson, Advances in Cancer Research, 11 (1968), pp. 223–226 & 240–241.
Regelson et al., Nature, 186: 778–780, (Jun. 1960).
Regelson, Polymeric Science and Technology 2: 161–168, (1973).
Breslow, Pure and Applied Chemistry, 46: 103–113, (1976).
Hodnett et al., J. Med. Chem. 17 (12) 1335–1337, (1974).

*Primary Examiner*—Frank Cacciapaglia, Jr.
*Attorney, Agent, or Firm*—Scott J. Meyer; James W. Williams, Jr.

[57] ABSTRACT

The disclosure relates to a method of producing an immune response in a warm-blooded animal comprising administering to said animal from about 0.1 to about 100 mg/Kg of body weight of a composition selected from the group consisting of a copolymer of olefin monomer and polycarboxylic anhydride having an average molecular weight of from about 300 to about 1500 in which said copolymer is derivatized to contain (a) half-amide, half-carboxyl acid groups and (b) imide groups in which said imide groups comprise from about 5% to about 40% by weight of said derivatized groups, and the pharmaceutically acceptable cationic salt derivatives of said derivatized copolymers.

7 Claims, 3 Drawing Figures

METHOD OF PRODUCING IMMUNE RESPONSE BY ADMINISTERING POLYMERIC COMPOSITION

CROSS-REFERENCE TO RELATED APPLICATIONS

This is a continuation-in-part of application Ser. No. 5,638, filed Jan. 22, 1979, now U.S. Pat. No. 4,255,537, and claims the right of priority in part from New Zealand Application Ser. No. 192 649-80, filed Jan. 18, 1980.

This invention relates to polymeric compounds which are useful for administration as immunoregulatory agents in warm-blooded animals.

It is well-known that certain substances have utility as immunoregulants. Examples of such substances are *Corynebactirum parvum*, Bacillus Calmette-Guerin, a viable strain of *Mycobacterium bovis*, glucan, and the synthetic compounds levamisole, tilorone and isoprinosine. Some of these substances show activity as immune stimulants of the reticulo-endothelial system while others act as immune suppressants. Still others may act in either capacity depending in part upon the dosage and frequency of administration.

Synthetic polyanions such as pyran (a copolymer of divinyl ether and maleic anhydride-DIVEMA) and copolymers of ethylene and maleic anhydride (EMA) also have been described heretofore as useful for producing an immune response upon administration to warm-blooded animals. See, e.g. Hodnett and Tien Hai Tai, *J. Med. Chem.* 17. (12), 1335-57 (1974), and Breslow, *Pure & Appl. Chem.* 46, 103-13 (1976). These polyanions generally are polymeric materials having relatively high molecular weights of several thousand and upward.

In accordance with the present invention, novel polymeric compounds have been synthesized which are useful for administration as immunoregulatory agents in warm-blooded animals. These compounds are copolymers of olefin monomers having from about 2 to about 4 carbon atoms and α,β-unsaturated polycarboxylic anhydrides having from 4 to about 6 carbon atoms, having an average molecular weight of from about 300 to about 1500, and derivatized to contain both (a) half-amide, half-carboxyl acid groups and (b) imide groups in which said imide groups comprise from about 5% by weight to about 40% by weight of said derivatized groups, or the pharmaceutically acceptable cationic salt derivatives of said derivatized copolymers. The base copolymer preferably has an average molecular weight of about 850 and the imide groups preferably comprise from about 10% to about 25%, and most preferably about 20%, by weight of said derivatized groups.

Illustrative examples of the foregoing olefin monomers are ethylene, propylene and isobutylene; illustrative examples of the foregoing polycarboxylic anhydrides are maleic anhydride, citraconic anhydride and aconitic anhydride. Of these monomeric components, ethylene and maleic anhydride are preferred. Illustrative examples of the copolymers are copolymers of propylene and maleic anhydride, copolymers of ethylene and citraconic anhydride and the preferred copolymers of ethylene and maleic anhydride. Illustrative examples of the pharmaceutically acceptable cationic salt derivatives are the sodium, potassium and preferably ammonium salt derivatives.

For purposes of illustration and not limitation, the preferred copolymer of ethylene and maleic anhydride as appropriately derivatized can be represented as having the following structural units or groups:

(a) half-amide, half-carboxylate salt

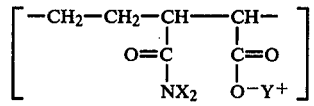

and (b) imide

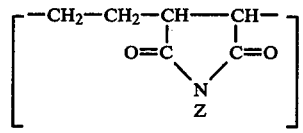

wherein
X=H
Y=H, ammonium or a pharmaceutically acceptable metal cation, and preferably ammonium; and
Z=H, ammonium or a pharmaceutically acceptable metal cation, and preferably H.

The respective (a) and (b) units or groups are distributed along a substantially linear continuous carbon atom molecule. From about 5% to about 40% of these units should be imide with the balance being principally half-amide, half-carboxylate salt units. These units can be positioned randomly within the chain and/or randomly within the polymer. It will be appreciated that a small portion (believed to be less than 10%) of monoammonium carboxyl or other pharmaceutically acceptable salt group and/or dicarboxyl group also can be present as may arise from partially reacted or unreacted anhydride during the preparation of these compounds.

Of the foregoing derivatized groups, the (a) half-amide, half-carboxylate salt group preferably is half-amide, half-ammonium salt, and the (b) imide group preferably is unsubstituted imide.

Again, for purposes of illustration and not limitation, the preferred copolymer of ethylene and maleic anhydride as preferably derivatized can be represented as having the following structural units or groups:

(a) half-amide, half-ammonium salt

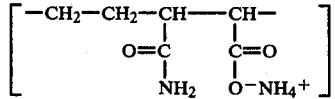

and (b) unsubstituted imide

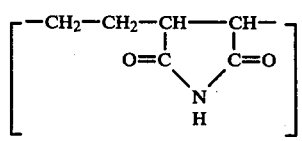

As before, the respective (a) and (b) units or groups are distributed along a substantially linear continuous carbon atom molecule. From about 5% to about 40% of these units are preferably unsubstituted imide with the balance being principally the preferred half-imide, half-ammonium salt units. These units can be positioned randomly within the chain or randomly within the polymer. It will be appreciated that a small portion (believed to be less than 10%) of monoammonium carboxyl or dicarboxyl group can be present as may derive from partially reacted or unreacted anhydride during the preparation of these compounds.

The polymeric immunoregulatory agents of this invention also preferably are water soluble.

The invention is further illustrated by the accompanying drawings in which.

Figure 1:
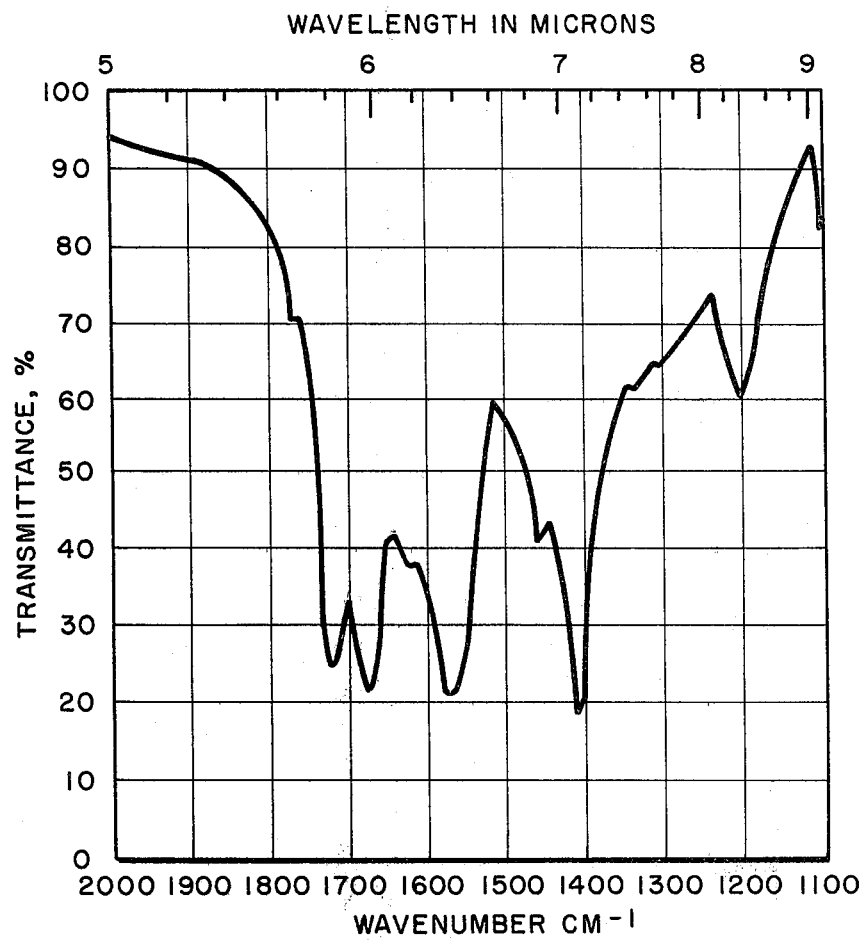
FIG. 1 shows the fingerprint region of the infrared absorption spectrum of a representative polymer of this invention which is derivatized to contain 20% imide. See Example 3, Table IV, Run 5, below.

The underivatized low molecular weight copolymers which are used to prepare the desired immunoregulatory agents of this invention can be prepared by well known methods as described, for example, in U.S. Pat. Nos. 2,857,365; 2,913,437; 2,938,016; and 2,980,653. Typically, the olefin, for example ethylene, is reacted with the polycarboxylic anhydride, for example maleic anhydride, at temperatures ranging from about 40° C. to about 100° C. in the presence of a free-radical promoting catalyst and a liquid solvent that is a solvent for the reactants and a nonsolvent for the interpolymer formed. Conventional peroxide type and azo type free-radical promoting polymerization catalysts are eminently suitable for this purpose, and benzoyl peroxide, for example, is preferred. Inert solvents such as benzene, halobenzenes, and haloparaffins are useful solvents for the polymerization reaction. However, an alkylated aromatic hydrocarbon having at least one α-hydrogen, such as for example ethyl benzene, isopropyl benzene, diisopropyl benzene, toluene, or xylene, is a preferred liquid medium for the polymerization reaction for the purpose of reducing the molecular weight of the copolymer product as described in U.S. Pat. No. 2,913,437. Ethyl benzene is especially preferred as the liquid medium for the latter purpose. The copolymer preferably contains substantially equimolar quantities of the olefin residue and the anhydride residue such as will be obtained by the use of about equimolar quantities of the reactant monomers. The resulting copolymer product is obtained in solid form and is easily recovered by filtration, centrifugation and the like separation procedures.

It will be appreciated that the free-radical initiator, both through initiation of the polymerization reaction and subsequent termination or telomerization with the alkylated aromatic hydrocarbon liquid medium, will cause the introduction of various organic moieties into the polymeric structure. The percentage of these moieties in the total polymer composition will increase as the molecular weight of the polymer is decreased. For example, use of benzoyl peroxide as the free-radical initiator and ethyl benzene as the liquid reaction medium will cause introduction of their respective aromatic moieties into the polymeric structure. These moieties will constitute a higher percentage of the total structure of the polymers having about 300 molecular weight than the polymers having about 1500 molecular weight.

It will be further recognized that in the preparation of these low molecular weight copolymers a certain amount of cross-linking agent can be incorporated into the copolymer to thereby render the product insoluble in water. Examples of such cross-linking agents are vinyl and allyl esters, especially the acrylates and crotonates as described in U.S. Pat. No. 3,165,486. The copolymers also can be insolubilized after derivatization, by various means such as, for example, cross-linking with diamine as described in U.S. Pat. No. 3,554,985, or by attachment to carriers such as bentonite, latex particles, or erythrocytes.

It is known that amide derivatives of the EMA type copolymers can be prepared by reacting the copolymer with ammonia gas at ordinary or elevated temperatures as described in Canadian Pat. No. 664,326 and in U.S. Pat. Nos. 2,883,287 and 3,157,595. It is also known that reaction at higher temperatures tends to promote imide formation, while reaction in inert organic liquid solvent media such as benzene can be used to control the reaction temperature and retard imide formation. Another known method for amide formation comprises reaction of the polymer in liquid ammonia at −33° C.

Figure 2:
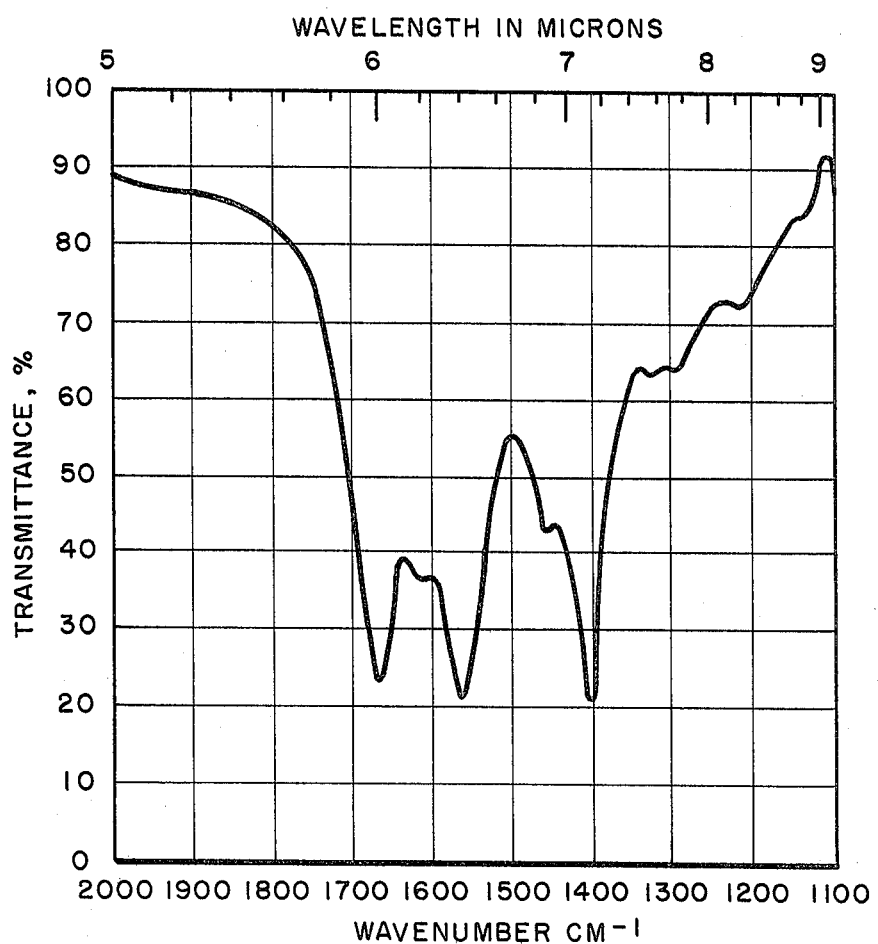
FIG. 2 shows for comparative purposes the fingerprint region of the infrared absorption spectrum of a corresponding polymer which contains 0% imide. See Example 2(a) below.

While the aforesaid procedures are generally useful for preparation of the half-amide, half-ammonium salt as an intermediate step to preparation of the imide containing derivatives, they are deficient from a time-diffusion effect of ammonia into the inner core of the EMA particles for purposes of this invention as described in Example 2, below. A preferred method for purposes of the present invention comprises first dissolving the EMA type copolymer in acetone followed by reaction of the dissolved polymer with liquid ammonia in acetone. The desired half-amide, half-ammonium salt product precipitates out of solution and then can be readily recovered by filtration, centrifugation and the like separation procedures as illustrated further in Example 2, parts a, b and c, below. FIG. 2 of the accompanying drawings shows the infrared spectrum of the half-amide, half-ammonium salt product of said Example 2(a), which contains 0% imide.

Preparation of the desired imide containing derivative then can be obtained by reacting the intermediate half-imide, half-ammonium salt with ammonia in suitable organic solvent media such as, for example, toluene or xylene, at refluxing temperatures until the desired percentage of imide derivative is formed as illustrated further in Examples 3 and 4, below.

FIG. 1 of the accompanying drawings shows the infrared spectrum of a representative example (Example 3, Table IV, Run 5) of the desired polymer which is derivatized to contain both (a) the half-amide, half-ammonium salt function and (b) the imide function, and in which the imide comprises 20% of said derivatization. The polymer of this example has an average molecular weight of about 850 and the 20% imide lies within the preferred range of about 10% to about 25% imide.

Figure 3:
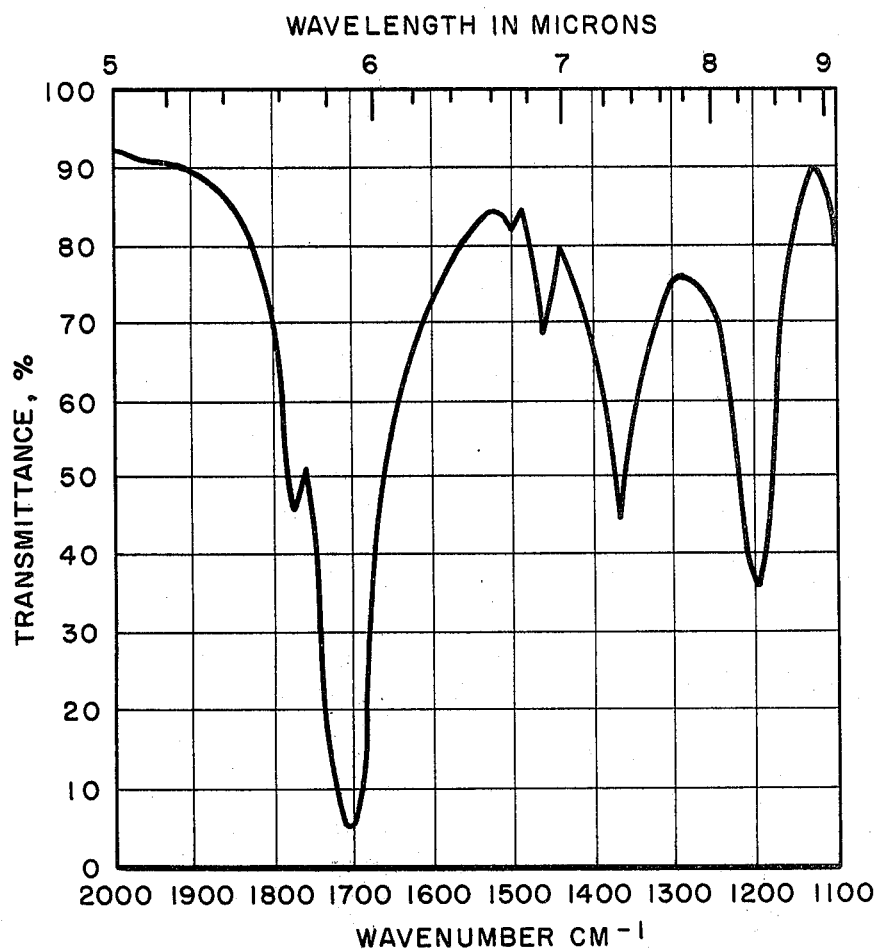
FIG. 3 shows for comparative purposes the fingerprint region of the infrared absorption spectrum of a corresponding polymer which is derivatized to contain 100% imide. See Example 5, below.

For purposes of comparison, a full 100% imide derivative of the EMA copolymer also was prepared as illustrated in Example 5, below. FIG. 3 of the drawings shows the infrared spectrum of this polymer.

A detailed description of the infrared analysis for identification of the various aforesaid functional groupings as illustrated in FIGS. 1 to 3 is set forth below, following Example 1.

The ability of compounds according to the above description to affect the immunoregulatory mechanism or to provide an immune adjuvant effect in a host mammal was measured by their ability to stimulate the production of antibodies according to standard procedure for such measurement. Thus, in one series of tests, these compounds were tested in normal Lewis strain rats and found to have ability to stimulate immune responses in terms of increasing 19-S (IgM) antibody producing cells to heterologous erythrocytes (Sheep Red Blood Cels, SRBC) by the standard Jerne Plaque Assay Method. See, e.g. J. T. Barrett, "Textbook of Immunology", C. V. Mosby Company, 1978, and H. N. Eisen, "Immunology", Medical Department, Harper and Row Publishers, Inc., 1974.

In another series of tests, these compounds were tested in normal Lewis strain rats in which the normal thymic function was removed by adult thymectomy (Tx), which was surgically performed at the age of 8 to 12 weeks, and high doses of total body irradiation (TBI) followed by bone marrow cell repopulation (BM). Thymectomy, total body irradiation and bone cell repopulation were all done by standard procedures as described by Falk et al., Surgery 84 (4), 483–489 (1978); Abstract, Canadian Society for Clinical Investigation, Jan. 24–27, 1978, Vancouver, Canada; and Abstract, Royal College of Physicians and Surgeons, Jan. 25–28, 1978, Vancouver, Canada. Six weeks thereafter, the IgM antibody response to SRBC upon administration of these compounds showed activity without the presence of T-cells, thereby indicating antibody activation through the B-cells. T-cells are thymus-derived lymphocytes whereas B-cells are lymphocytes which differentiate in the bursal equivalent or bone marrow.

Although immunoregulatory activity is illustrated herein in rats using sheep erythrocytes as the antigen, it should be understood that substantially similar activity can be shown against any foreign protein (antigen) in any warm blooded animal. Rats and SRBC are used in the illustrative examples herein for their convenient availability and ready adaptability to standard laboratory test procedures.

The compounds described above can be administered to a warm-blooded animal by a variety of conventional routes, especially intravenously or intraperitoneally, in dosages ranging from about 0.1 to about 100 mg/Kg of body weight. Such administration preferably is in aqueous solution such as sterile water or physiologically normal saline. Orally, they can be administered in the form of tablets, powders, capsules, elixers and the like dosage forms in admixture with common solid and liquid diluents, carriers, suspending agents and adjuvants such as, for example, cornstarch, lactose, talc, stearic acid, magnesium stearate, gelatin, acacia and locust bean gums, alcohol, water, dimethylsulfoxide (DMSO), vegetable oils and the like materials. The oral dosage form preferably is solid reconstituted in a suitable liquid mixture at the time of administration in order to maintain stability of the dual groupings of (a) half-amide, half-carboxyl acid and (b) imide. Other suitable dosages of the polymers to produce a desired immunoregulatory effect can be determined by reference to the specific examples set forth hereinafter. Generally, small doses will be administered initially and these may be increased gradually to determine the optimum immunostimulatory effective amount in terms of the dosage and frequency of administration for the particular subject.

Although the following detailed examples will further illustrate the invention, it will be appreciated that the invention is not limited to these specific examples.

EXAMPLE 1

Preparation of EMA

The desired raw material ethylene/maleic anhydride (EMA) copolymer was prepared in a heated one-gallon stainless steel reactor fitted with internal water cooling coil, magnetic driven stirrer operating optimally at 1000–1200 r.p.m., ethylene inlet and an inlet through which additional catalyst could be added in solution pressured in by ethylene. Samples could be withdrawn or the final contents emptied through a bottom port. Auxilliary equipment for heating and cooling control were provided. In a typical run the charge to the reactor consisted of 1625 g. (1875 ml) ethylbenzene, 190 g. (1.94 mole) maleic anhydride, and 14.1 g. (0.058 mole) benzoyl peroxide dissolved in 80 g. (92 ml) ethylbenzene. The catalyst vessel was washed into the reactor with an additional 20.0 ml ethylbenzene. The reactor was closed and pressure vented twice with ethylene at room temperature to displace air in the system. Thereafter the temperature was brought to and held at 70° C. with an ethylene feed pressure of 200 p.s.i. for the duration of the polymerization. After three hours polymerization at 70° C. and 200 p.s.i. ethylene pressure an addition of 9.4 g (0.039 mole) benzoyl peroxide in 60 g (70 ml) ethylbenzene was made through the catalyst addition line followed by a wash of this inlet with 20 ml ethylbenzene. Stirring with heating at 70° C. at 200 psi. ethylene feed was then continued for an additional 14 hours to complete the polymerization. At the end of the run the reactor was cooled and vented and the contents consisted of an ethylbenzene slurry of product ethylene/maleic anhydride (EMA) copolymer and a small amount of product EMA glazed on the stirrer, cooling coils and reactor surfaces. This slurry was filtered, after combining with the glazed material removed by scraping, and the conversion of maleic anhydride was determined on the filtrate by NaOH titration to a phenolphthalin end point.

The total EMA product workup consisted of filtration, slurry extraction three times (1 hour each) with 2 liters xylene at room temperature followed by three extractions (1 hour each) with 2 liters hexane and final filtration. Filtration was employed between all extraction steps. The final EMA product was vacuum dried overnight with full oil pump vacuum at 55°–60° C. The thus dried EMA product was pulverized in a Waring blender for 5 minutes to reduce the minor portion of glazed material to a powder consistency. Table I summarizes the results obtained on seven such consecutive EMA polymerizations.

TABLE I

| Run No. | Maleic Anhydride Conversion % | EMA Product Recovery g. (% Yield) | Hydrogen % (1) | Carbon % (1) | Specific Viscosity 1% DMF at 25° C. | Equivalent Weight (3) |
|---|---|---|---|---|---|---|
| A | 91.5 | 185 (68.8) | 4.98 | 57.34 | 0.064 | 138.5 |
| B | 98.6 | 227 (83.6) | 5.03 | 58.11 | 0.068 | 139.9 |
| C | 98.3 | 223 (82.1) | 5.10 | 58.15 | 0.063 | 140.0 |
| D | 98.3 | 219 (81.1) | 5.04 | 58.24 | 0.066 | 139.1 |
| E | 97.9 | 223 (81.7) | 5.10 | 57.89 | 0.063 | 140.6 |

TABLE I-continued

| Run No. | Maleic Anhydride Conversion % | EMA Product Recovery g. (% Yield) | Hydrogen % (1) | Carbon % (1) | Specific Viscosity 1% DMF at 25° C. | Equivalent Weight (3) |
|---|---|---|---|---|---|---|
| F | 97.9 | 225 (81.9) | 5.12 | 58.14 | 0.061 | 141.5 |
| G | 98.6 | 224 (82.4) | 5.11 | 58.05 | 0.064 | 140.1 |

(1) Average of two determinations.
(2) Substantially in accordance with ASTM D-2515-74 procedure, Ostwald viscometer.
(3) Weight in grams containing one mole unit of anhydride determined by potentiometric pH titration of aqueous solution with standard NaOH.

Molecular weight parameters were determined on the product EMA using preparation F above as a typical product. The material was vacuum dried for 24 hours at 100° C. using oil pump vacuum. Parameters were determined in dry dimethyl formamide (DMF). For preparation F the number average molecular weight ($M_n$) was determined as 852 using Vapor Pressure Osmometry in DMF at 120° C. using a Knauer VP Osmometer. The weight average molecular weight ($M_w$) was determined as 5730 using low angle laser light scattering, again in DMF, employing a Chromatix KMX-6 instrument. Intrinsic viscosity in DMF at 25° C. was measured by capillary viscometry using a Cannon Ubblehode dilution viscometer (size 75) by extrapolation of four different concentrations to zero concentration. The intrinsic viscosity of preparation F was found to be 0.0607 dl/g.

Similar determinations of $M_n$, $M_w$ and intrinsic viscosity were made in identical fashion using an EMA preparation of higher specific viscosity (0.11, 1%, DMF, 25° C.) In this case the intrinsic viscosity was found to be 0.1227 dl/g, the $M_n$ was 2,264 and the $M_w$ was 12,970.

Using the above values for two EMA products of varying specific viscosity the K and $\alpha$ constants in the standard equation, relating intrinsic viscosity ($[\eta]$) to molecular weight, $[\eta] = KM^\alpha$, were determined. The found relationships were:

$$[\eta]_{25°DMF} = 4.71 \times 10^{-4} M_n^{0.72}$$

and $$[\eta]_{25°DMF} = 3.51 \times 10^{-5} M_w^{0.86}$$

The term "average molecular weight" as used herein with respect to the disclosed and claimed copolymers of this invention is defined to mean number average molecular weight.

Identification of Functional Groups

The identification of the various functional groupings for all of the polymeric derivative examples, both qualitative and quantitative, was accomplished by Infrared analysis using a Beckman IR-12 Spectrophotometer. Sample preparation, absorbance frequency assignments and procedures to determine the ratio of imide groups to amide groupings followed procedures set forth in either "The Infra-red Spectra of Complex Molecules", Bellamy, John Wiley and Sons, 1960, or "Practical Infrared Spectroscopy," Cross, Butterworth, 1964. Sample preparation, in all cases, utilized pressed discs of 2 mg polymer per 250 mg dry KBr composition with 70 mg of mixed polymer/KBr per disc. Absorbing band positions are quoted in units of wave number which are expressed in reciprocal centimeters ($cm^{-1}$), usually styled as band frequencies.

For qualitative "fingerprinting" of product composition as the presence or absence of certain groups the following band frequency assignments are accepted and were used:

| | Wave number ($cm^{-1}$) | Function |
|---|---|---|
| 1. 5-membered ring anhydride Doublet: | 1870–1830 minor<br>1800–1760 major | C=O stretch |
| 2. Undissociated aliphatic acid (COOH): | 1725–1700 | C=O stretch |
| 3. Polymeric imide, 5-membered ring Doublet: | 1715 major<br>1770 minor | C=stretch |
| 4. Polymeric primary amide: Amide-I band | 1670 major<br>1620 minor | C=O stretch<br>NH deformation and C—N stretch |
| 5. Carboxylate ion —$CO_2$— | 1560–1570 | asymmetric stretch |
| 6. Methylene —$CH_2$— | 1470–1450 | C—H deformation |
| 7. Ammonium ($NH_4^+$) salt of carboxylate (Intensity depends upon cation nature) | 1405–1400 | symmetric stretch |
| 8. Polymers with a high concentration of imide groups (over 60%) also contain a doublet: in addition to those shown in 3 above. | 1180–1200 major<br>1370–1350 minor | C—N stretch |

For quantitative estimation of the imide/amide content of a polymer containing both groups, in addition to ammonium carboxylate function, a ratio of the absorbancy intensity of the major imide band at 1715 $cm^{-1}$ to the major primary amide band at 1670 $cm^{-1}$ was determined. The imide content was determined by comparing the measured ratio of imide/amide (above) to a standard curve of percent imide vs imide/amide absorbance ratio prepared from a series of infra-red tracings obtained by mixing increasing amounts of pure (about 100%) imide (described in Example 5) with polymer containing no imide or unionized COOH but with only amide and ionized carboxyl (described in Example 2) functions.

For this latter test of imide/amide ratio, care was taken to be sure that unionized carboxyl was not present at 1715 cm$^{-1}$ by first dissolving the sample in water, adjusting the pH to 10.0 with ammonium hydroxide and freeze-drying to convert any unionized COOH to ammonium carboxylate. Such procedures increase the intensity of the carboxylate bands at 1560 and 1400 cm$^{-1}$ but insure that the remaining band at 1715 cm$^{-1}$ is indeed of imide origin.

In all the following examples references to the presence or absence of functional groups and to the imide content of imide containing polymers is made on the basis of the presence or absence of the above functional band assignments and the above method for estimating quantitative imide/amide band intensity ratios.

EXAMPLE 2

Preparation of Half Amide-Half Ammonium COO$^-$ Salt of EMA (AEMA)

Previous methods for the ammoniation of EMA polymers (disclosed in U.S. Pat. No. 3,157,595 and Canadian Pat. No. 664,326) by either of three methods: (1) dry ammoniation with ammonia gas at ordinary temperatures by sparging ammonia into vigorously stirred dry EMA powder, (2) sparging ammonia into a stirred slurry of EMA powder in benzene or hexane, or (3) by direct addition of solid EMA powder to a stirred excess of liquid ammonia to yield the half amide-half ammonium carboxylate salt of EMA have been found to be deficient for the present use. This deficiency relates to a substantial time-diffusion effect of ammonia into the inner core of even finely ground EMA particles. Even with prolonged reaction time the thusly prepared amide-ammonium salt products always contain residual amounts of unreacted anhydride, approaching 5 wt percent, as evidenced by the presence of anhydride absorbancy bands at 1780 and 1850 cm$^{-1}$ frequencies.

The following preferred method was developed to obviate long reaction periods and poor temperature control with the formation of products which contained no anhydride function.

(a) EMA polymer from Example 1-F (80 g) was dissolved in 800 ml acetone (AR-grade) and this solution was added over a 20 minute period to a stirred solution of 100 ml liquid ammonia in 3 liters acetone at −70° C. (Dry Ice-acetone bath). After the 20 minute addition period the total mixture was allowed to gradually warm to room temperature (4 hours) during which time the precipitated product color changed from an initial yellow to white. The product was filtered and successively slurried twice with 2 liters acetone followed by two slurries with 1.5 liters of 50/50 acetone/hexane. All slurry steps were for 30 minutes each. The final product was filtered and dried over night at 45° C. at 20-25 mm Hg vacuum. The dried product was dissolved in 900 ml water, filtered through a 0.45 micron filter and freeze dried to yield 98.7 g, 100% yield, of half amide-half ammonium carboxyl salt.

(b) Procedure (a) above was repeated as follows using EMA polymer from Example 1-F but with water added to the original EMA solution in acetone. The EMA (60 g) was dissolved in 500 ml acetone plus 2.32 g water and the solution was refluxed for 2 hours. The cooled acetone solution of EMA was added with stirring within a 10 min. period to 2 liters acetone containing 3 moles liquid ammonia at −60° C. As before the reaction slurry was allowed to warm to room temperature and worked up as above with 2 slurries in 1.5 liters acetone and one slurry with 1 liter hexane, filtered and vacuum dried at 40° C., 20-25 mm Hg overnight. The recovered dried product consisted of 84 g which was greater than 100% yield.

(c) A third preparation utilized EMA polymer from Example 1-G. 100 g (0.714 mole) EMA was refluxed for 2 hrs. in 700 ml. acetone containing 3.85 g water. The cooled acetone solution was added over a 10 minute period to a stirred solution of 3.3 liters acetone containing 60 ml liquid ammonia at −50° C. After one hour at −50° C. the reaction slurry was allowed to warm to room temperature (2 hours). The filtered product was slurried twice in 2 liters acetone (30 minutes each) and twice in 2 liters hexane (30 minutes each), filtered and dried overnight at 50° C. at full oil pump vacuum. The recovered dry half amide-half ammonium carboxyl salt was 115.6 g, 93% yield.

Analysis of the above three preparations is summarized in Table II.

TABLE II

| Preparation | a | b | c |
|---|---|---|---|
| Nitrogen, % (Avg. of 2) | 13.40 | 14.18 | 14.19 |
| Functional Composition by Infra red | | | |
| Anhydride | None | None | None |
| Undissociated COOH | None | None | None |
| Imide | None | None | None |
| Primary Amide | Major | Major | Major |
| Ionized COO$^-$ | Major | Major | Major |
| Methylene —CH$_2$— | Yes | Yes | Yes |
| —COO—NH$_4^+$ | Major | Major | Major |

EXAMPLE 3

Preparation of Partial Imide Derivatives in Xylene

A 10 g sample of the half amide-half ammonium carboxyl salt of Example 2a was slurried in 250 ml xylene in a 1 liter flask fitted with stirrer, thermometer, water take-off trap and a gas inlet sparger for ammonia. The slurry was refluxed for a period of 12 hours while maintaining a steady flow of ammonia through the gas inlet sparger and while removing water. Aliquot samples of product slurry were removed at various times (see Table III) for assay of conversion to imide versus time. Each small sample was worked up by three consecutive slurries in 100 ml hexane, filtered and dried at 50° C., 20-25 mm Hg vacuum. pH of 2% aqueous solutions was measured both before and after further solution in water, pH adjustment to 10.0 (NH$_4$OH) and freeze drying. Infra red was obtained on all samples to establish imide to amide ratios and thus percent imide content. The results are tabulated in Table III.

TABLE III

| Time of xylene reflux at sample removal | pH-1[a] | pH-2[b] | I/A ratio[c] | Imide[d] % wt. |
|---|---|---|---|---|
| 15 min. | 6.26 | 7.20 | 0.723 | 13.8 |
| 30 min. | 6.00 | 5.86 | 0.858 | 18.5 |
| 45 min. | 5.91 | 5.76 | 0.999 | 23.3 |
| 1 hr. | 5.78 | 5.53 | 1.113 | 27.4 |
| 1.5 hr. | 5.43 | 5.43 | 1.398 | 36.8 |
| 2 hr. | 5.27 | 5.76 | 1.501 | 40.2 |
| 3 hr. | 4.94 | 5.72 | 1.821 | 50.0 |
| 4 hr. | 4.78 | 5.38 | — | — |
| 6 hr. | 4.73 | 5.76 | — | — |
| 7.5 hr. | 4.73 | 5.60 | — | — |

TABLE III-continued

| Time of xylene reflux at sample removal | pH-1[a] | pH-2[b] | I/A ratio[c] | Imide[d] % wt. |
|---|---|---|---|---|
| 12 hr. | — | — | — | — |

[a] pH of 2% aqueous solution before pH adjustment.
[b] pH of 2% aqueous solution, adjusted to pH 10, and freeze dried.
[c] Ratio of IR band absorbance intensity at wave number 1715 cm$^{-1}$/1670 cm$^{-1}$.
[d] Obtained from standard curve of composition vs. I/A ratio.

A further set of nine individual experiments were run wherein half amide-half ammonium carboxyl salt of Example 2-b was used. Each individual run was refluxed in xylene slurry for the noted time (Table IV) and worked up in total.

The dry products from hexane washing were individually dissolved in 150 ml water, pH adjusted to 10.0 with NH₄OH, filtered through a 0.20 micron filter and directly freeze dried in sterile serum bottles for in vivo animal evaluation. The yields and analysis of the various runs are described in Table IV.

TABLE IV

| Run No. | Reaction Time at xylene reflux | Product yield[1] g. (% yield) | pH-1[a] | pH-2[b] | Nitrogen[c] % | I/A[d] ratio | Imide[e] % |
|---|---|---|---|---|---|---|---|
| 1. | 2 min. | 4.45 (90.1) | 5.08 | 7.08 | 14.27 | 0.489 | 5.3 |
| 2. | 4 min. | 3.92 (92.6) | 4.85 | 6.93 | 14.28 | 0.559 | 7.9 |
| 3. | 10 min. | 7.87 (80.5) | 4.43 | 7.12 | 14.48 | 0.661 | 11.5 |
| 4. | 20 min. | 6.28 (81.1) | 4.52 | 6.74 | 13.82 | 0.798 | 16.5 |
| 5. | 30 min. | 6.15 (80.1) | 3.99 | 6.39 | 13.67 | 0.911 | 20.4 |
| 6. | 45 min. | 6.30 (82.7) | 4.60 | 6.69 | 13.71 | 1.020 | 24.1 |
| 7. | 1 hr. | 6.30 (83.4) | 4.70 | 6.22 | 13.80 | 1.139 | 28.2 |
| 8. | 1.5 hr. | 6.15 (82.6) | 4.37 | 6.00 | 13.07 | 1.333 | 34.7 |
| 9. | 3.0 hr. | 5.90 (81.9) | 4.33 | 5.81 | 12.52 | 1.828 | 50.1 |

[1] Run 1 used 5.0 g AEMA, 2 used 4.3 g, 3 used 10.0 g, rest used 8.0 g.
[a] pH of 2% acqueous solution before pH adjustment.
[b] pH of 2% aqueous solution, adjusted to pH 10.0 and freeze-dried.
[c] Obtained on pH adjusted freeze-dried product.
[d] See footnote (c) Table III-freeze-dried product.
[e] See footnote (d) Table III-freeze-dried product.

EXAMPLE 4

Preparation of Partial Imide Derivatives in Toluene

Partial imides of half amide-half ammonium carboxyl salt of EMA polymer were prepared essentially as in Example 3 except that imide formation rate was varied by operating at toluene reflux (110° C.) in toluene slurry instead of xylene as in Example 3.

The EMA used was from Example 1-F and the procedure used for preparation of the half amide-half ammonium salt was the same as Example 2a without added water. This product showed major IR absorption bands for primary amide, ionized carboxyl and ammonium carboxylate with no evidence of anhydride or imide. 28 g of this amide ammonium salt was slurried in one liter toluene and heated to reflux. Three aliquots were removed at 2 hours, 3.5 hours and 5 hours reflux time (end of run). The products were isolated by filtration, 3 slurries in 150 ml toluene and 3 slurries in petroleum ether and vacuum dried, 25 mm Hg. for 17 hours at room temperature. The dry products were then dissolved in 100 ml water, adjusted to pH 9.0 with NH₄OH, filtered through a 0.20 micron filter and directly freeze dried in sterile serum bottles for in vivo animal evaluation. Results were obtained as follows:

| Toluene Reflux Time, hr. | Product g. | Nitrogen % | I/A[a] ratio | Imide[b] % |
|---|---|---|---|---|
| 2 | 6.15 | 13.78 | 0.531 | 6.5 |
| 3.5 | 7.73 | 13.41 | 0.600 | 9.5 |
| 5 | 9.24 | 13.82 | 0.647 | 11.0 |

[a] See footnote (c) Table III - freeze-dried product
[b] See footnote (d) Table III - freeze-dried product

EXAMPLE 5

Preparation of Full Imide of EMA EMA Sp. Visc.=0.061

The full imide of EMA was prepared by refluxing 20 g of the product from Example 2a in 250 ml xylene slurry for 18.5 hours under a constant flow of ammonia and by removing water of reaction in a Dean Stark trap. A total of 2.7 ml of water was removed in the trap. The product was filtered, slurried with hexane three times and dried overnight, 25 mm Hg in vacuum at room temperature. The dry product weighed 13.5 g, 84.3% yield. Three grams of the product was stirred in 150 ml water overnight, filtered, washed with water and freeze dried. The product had a nitrogen content of 9.53% and an IR scan exhibited absorption bands only at 1190, 1360, 1715 and 1770 cm$^{-1}$ wave numbers, typical of imide functionality. No amide, anhydride, ionized carboxyl or ammonium carboxylate absorption bands were evident.

The above full imide product was used in various admixtures with the non-imide containing half amide-half ammonium carboxylate salt from Example 2a to establish a master imide/amide infra red composition curve as previously described following Example 1 as follows: The noted amounts, weighed on an analytical balance, were mixed in stainless steel mixers using a Wigglebug Mixer. Infrared scans were determined on pressed discs of the above mixtures with dry KBr using 2 mg polymer mixture to 250 mg KBr. The pellet consisted of 70 mg of polymer/KBr mix per disc. The total master curve was constructed from the following mixed compositions:

| Weight Complete Imide from Example 5. mg. | Weight of Zero % Imide from Example 2a mg. | Imide/Amide absorbancy ratio |
|---|---|---|
| 3 | 97 | 0.427 |
| 6 | 94 | 0.509 |
| 10 | 90 | 0.621 |
| 20 | 80 | 0.843 |
| 30 | 70 | 1.161 |

-continued

| Weight Complete Imide from Example 5. mg. | Weight of Zero % Imide from Example 2a mg. | Imide/Amide absorbancy ratio |
| --- | --- | --- |
| 40 | 60 | 1.519 |
| 50 | 50 | 1.871 |
| 60 | 40 | 2.099 |
| 70 | 30 | 2.564 |
| 80 | 20 | 3.008 |

EXAMPLE 6

Preparation of Half Amide-half Ammonium COO⁻ salt of EMA by Prior Art Methods With and Without Water (a) A 500 ml 4-neck flask was fitted with Teflon stirrer, thermometer, gas inlet sparger and gas outlet bubbler. The ammonia inlet gas was run through a flow meter to follow rate of flow only on a qualitative basis. To the flask was charged 25 g. of EMA from Example 1D and the powder was stirred at a rate of 500 rpm. The ammonia inlet flow was held at a rate to attain 70° C. starting from room temperature without the use of a heating mantle. With 9 min. the powder temperature had reached 70° C. and ammonia flow was lowered to maintain this temperature. A temperature of 70° C. was maintained for 1 hr. 30 min. at which time ammonia was shut off and the reaction cooled under nitrogen. The yield of dry ammoniated EMA as half amide-half ammonium carboxylate was 30.8 g., 98.8% yield. The nitrogen percent was 14.01, 14.18 and a 2% aqueous solution pH was 6.07. IR scans indicated absorption bands for:

| Unreacted anhydride | at 1780 and 1850 | (less than 5% estimated) |
| --- | --- | --- |
| Primary amide | at 1670 and 1620 | (major) |
| Carboxylate ion | at 1565 | (major) |
| NH$_4^+$ carboxylate | at 1405 | (major) |
| Imides | None | |

(b) A second ammoniation of EMA from Example 1D was made as in (a) above except that the EMA was first treated with water as described below to enhance reaction with ammonia and lower the anhydride component in the product. 25 g. EMA was stirred at 500 rpm at 40° C. (heating mantle) for 6 hours in the presence of 0.53 g (17 mol%) water which was added dropwise over the initial twenty minutes from a 1.0 ml syringe. After 6 hours the powder was cooled to room temperature and ammoniation was carried out as in (a) above, allowing the temperature to reach 70° C. in ten minutes. The total ammoniation time at 70° C. was one hour and the product was cooled under nitrogen. The yield was 31.4 g., 100.8% yield, percent nitrogen was 14.02, 13.94, and the 2% aqueous solution pH was 6.45. IR scans indicated the following absorption bands:

| Unreacted anhydride | - present but much less than in (a) |
| --- | --- |
| Primary amide | Major as in (a) |
| Carboxyl ion | with NH$_4^+$ carboxylate |
| NH$_4^+$ carboxylate | being increased over (a), |
| Imide | - absent |

EXAMPLE 7

Characterization of Products Previously Prepared Substantially as in Example 6

During the period of July 1956 through February 1960 the half amide-half ammonium carboxylate salt derivatives of several viscosity grades (different molecular weights) of EMA were made and evaluated. The viscosity grades, in terms of specific viscosity at 1.0 wt.% in DMF at 25° C., used ranged from 1.19, 0.60, 0.11 to 0.060. The estimated molecular weight ($M_n$) corresponding values were 50–60,000; 20–30,000; 2–3,000 and 1000. The first three, i.e. using EMA of 0.11, 0.60 or 1.19 were ammoniated in large Pilot Plant equipment yielding product amounts of 600–800 pounds. The lower viscosity (0.060) EMA was ammoniated in smaller laboratory equipment using 200–300 grams of EMA. The procedures are described below, followed by product characterization obtained at that time.

Pilot Plant procedure synopsis (for 1.19, 0.60 and 0.11 sp. visc. EMA): The "ammoniation" vessel used was a jacketed stainless steel Stokes rotary dryer, Model 59AB fitted with proper means to introduce dry steam and anhydrous ammonia above the contents surface, a stirrer operating at 5.7 rpm. and a rotary valve for sealing the bottom and discharging the final product. The "full" volume of the unit was 40 cu. ft., the "working" volume was 27 cu. ft and the jacketed area was 63 sq. ft. In a typical run the ammoniator was closed at the bottom and 500–600 pounds of the appropriate viscosity EMA was charged with the stirrer running. The EMA was heated to 55° C. after which it was pre-hydrolyzed to the extent of 0.15–0.20 mols of water per mol of EMA by "above surface" addition of dry steam at the rate of 0.007 pounds of steam per pound of EMA over a 3-hr. period. During this period, the temperature was maintained between 55° and 70° C. by use of cooling water in the jacket. Anhydrous gaseous ammonia was then admitted to the reactor (above the surface of the partially hydrolyzed EMA) at a rate such that the temperature was maintained between 60° and 70° C. (about 5–8 pounds per hr.) until 2.0 mols of ammonia per mole of EMA had been added. After all ammonia was added the product was cooled to below 50° C. and dumped into storage containers.

Laboratory procedure for 0.06 sp. visc. EMA: The starting EMA was prepared in similar fashion to that described in Example 1 except that the reactor charge consisted of 267 g maleic anhydride, 2089 ml ethylbenzene, 45.8 ml n-butyraldehyde and 13.20 g. benzoyl peroxide added all at the beginning. The ethylene pressure was maintained for 24 hrs. at 200 psi at 70° C. The yield of final worked up product EMA was 279, 73.3% yield, and the specific viscosity was 0.060 at 1% in DMF at 25° C. To a 5-liter 4-neck flask was charged 249 g of 0.060 sp. visc. EMA solid powder and this was vigorously stirred for 6 hours at 45–55° C. after the initial dropwise addition of 5.3 g water (15 mol% based on EMA) to effect partial hydrolysis. Ammoniation was started using dry anhydrous ammonia gas sparged into the vigorously stirred solid EMA powder and the temperature was maintained at 31°–32° C. for 18 hours. During this period a slow but steady uptake of ammonia was observed. The final product weighed 320 g., 103.3% yield.

Product characterization of all of the above products is described in Table V below.

TABLE V

| Identification: | D | C | B | A |
|---|---|---|---|---|
| EMA used, sp. visc.[1] | 1.19 | 0.60 | 0.11 | 0.060 |
| Molecular Weight Range: | 50–60,000* | 20–30,000* | 2300** | 1060** |
| Ammoniated Product: CRD Code: | S-24 | 334 | 333 | 337 |
| Year prepared: | 1957 | 1957 | 1956 | 1960 |
| Nitrogen % | 15.83 | 16.86 | 14.80 | 13.83 |
| Infra red characterization: | | | | |
| Date Run: | — | 5/22/59 | 6/8/59 | 7/5/60 |
| Anhydride | — | Absent | Absent | Absent |
| Carboxylic acid (COOH) | — | Absent | Absent | Absent |
| Imide | — | Absent | Absent | Absent |
| Primary amide | — | Present | Present | Present |
| Carboxylate ion ($CO_2^-$) | — | Present | Present | Present |
| Ammonium carboxylate | — | Present | Present | Present |

[1] 1% DMF, 25° C.
*Estimated $M_n$ from viscosity - $M_n$ curve relationship.
**Determined December, 1960 by the ebulliometric method, boiling point raise in acetone.

Samples of the half amide-half ammonium carboxylate salts of EMA prepared in 1957–1960 and characterized at that time as described in Table V were stored in glass jars with ordinary screw caps (not under nitrogen nor sealed in any way) until early 1977 in a general purpose warehouse. At this time (1977) they were removed for continued evaluation (see Examples 8 and 10). Before reuse the materials were recharacterized with results shown in Table VI.

It is evident from the characterization data that the polymer products prepared in 1957–1960 which contained no imide at that time, had lost both ammonia and water and were thereby converted to imide-containing polymer products during the long storage.

TABLE VI

| Ammoniated Product Identification Code: | S-24 | 334 | 333 | 337 |
|---|---|---|---|---|
| Correspondence to Table V | D | C | B | A |
| Nitrogen, % | 14.02 | 12.46 | 12.53 | 12.62 |
| Infra-red characterization: | | | | |
| Date Run: | 1977 | 1978 | 1977 | 1977 |
| Anhydride | Absent | Absent | Absent | Absent |
| Carboxylic Acid (COOH) | Absent | Absent | Absent | Absent |
| Imide | Present | Present | Present | Present |
| Primary Amide | Present | Present | Present | Present |
| Carboxylate ion ($CO_2^-$) | Present | Present | Present | Present |
| Ammonium carboylate | Present | Present | Present | Present |
| Imide/Amide Absorbance ratio | 0.890 | 0.922 | 1.180 | 0.950 |
| Imide, % | 19.5 | 20.7 | 29.5 | 21.7 |

EXAMPLE 8

The direct toxicity of imide containing polymer from Example 7-VI-A was determined on normal male Fischer (F344) rats. Both I.P. and I.V. injection of polymer consisted of approximately 1 ml of physiological saline containing the appropriate quantity of polymer. To determine toxicity, polymer at doses of 100 mg/kg with increasing increments of 100 mg/kg up to 1000 mg/kg were given to five animals in each dose group. Polymer was administered both intraperitoneally and intravenously. No toxicity or animal deaths were observed with animals utilizing the intraperitoneal route up to 30 days of observation on a total of 50 rats. Toxicity was, however, observed when polymer was given in doses of 800 mg/kg (I.V. route) and over. One out of five animals at 800 mg/kg, two out of five animals at 900 mg/kg and four out of five animals at 1000 mg/kg appeared to develop convulsions upon intravenous administration of polymer and died. No toxicity or deaths were noted in animals given I.V. doses of 700 mg/kg or less over the 30 day observation period (35 animals).

After the 30 day observation period the 85 surviving rats were sacrificed and the brain, lung, heart, liver, kidney and spleen from each rat subjected to gross and microscopic pathology. No drug associated abnormalities were observed in any of the organ tissues.

In another study the toxicity of the above polymer administered I.P. was compared to that administered orally. The polymer from Example 7-VI-A was administered at doses of 100 mg/kg, 500 mg/kg and 1000 mg/kg either by injection (I.P.) or by gavage (P.O.) to each of five Fischer rats per dose group. The rats were observed for 14 days and no deaths or toxic manifestation occurred. After 14 days all animals were sacrificed, both from I.P. and P.O. drug administration, and the brain, lung, heart, liver, kidney and spleen from each animal subjected to gross and microscopic pathology. Again no abnormalities were observed in any of the organ tissues.

EXAMPLE 9

Polymers of the invention as described in Examples 3 and 4 were evaluated in normal Lewis rats for their ability to stimulate immune responses in terms of increasing 19-S (IgM) antibody producing cells to heterologous erythrocytes (Sheep Red Blood Cells, SRBC) by the standard Jerne Plaque assay method. See: "Textbook of Immunology", J. T. Barrett, C. V. Mosby Company, 1978 and "Immunology", H. N. Eisen, Medical Department, Harper and Row Publishers Inc., 1974. In a typical test an animal, in this case Lewis rats, is immunized with one ml of a 1:5 dilution of washed SRBC in physiological saline via the tail vein. At the same time the animals are given I.P. injections of the indicated polymer in one ml physiological saline. After 4 days spleen cells from the immunized animals are plated in an agarose tissue culture system with SRBC. The tissue culture medium supports the growth and excretion of antibody by the antibody-synthesizing cells. These antibodies diffuse from the originating cell and attach to neighboring erythrocytes. Serum compliment (normal guinea pig serum) is added promoting lysis of the RBC that have become coated with antibody forming a clear area, or plaque, around the antibody-forming cell. Such plaques (PFC) are counted and expressed as numbers of PFC per $1 \times 10^6$ spleen cells. The results are summarized in Table VII. All polymer compositions in Table VII were tested at 30 mg/kg.

TABLE VII

| Polymer Source from Example No. | Percent Imide from IR Imide/Amide ratio | Total Animals in Average | IgM PFC/ 1 × 10⁶ Spleen Cells | Stimulation Index Control = 1.00 |
|---|---|---|---|---|
| None (Control) | — | 16 | 568 | 1.00 |
| 2a | 0 | 10 | 1564 | 2.75 |
| 3-IV-1 | 5.3 | 6 | 1446 | 2.54 |
| 4 | 6.5 | 6 | 1478 | 2.60 |
| 3-IV-3 | 11.5 | 10 | 1620 | 2.86 |
| 3-IV-4 | 16.5 | 10 | 1770 | 3.12 |
| — | 16.0 | 6 | 1866 | 3.28 |
| 3-IV-6 | 24.1 | 10 | 1968 | 3.46 |
| — | 24.4 | 6 | 1984 | 3.49 |
| 3-IV-7 | 28.2 | 10 | 1992 | 3.51 |
| — | 32.6 | 6 | 1268 | 2.23 |
| 3-IV-8 | 34.7 | 10 | 1664 | 2.93 |
| 3-IV-9 | 50.1 | 10 | 926 | 1.63 |

TABLE VIII

IgM Antibody Response of Lewis Rats

| Polymer | Animal Treatment | Number of Animals | Dose mg/kg Route | Mean Response IgM~ PFC/1 × 10⁶ Spleen Cells | Stimulation Index Control = 1.00 |
|---|---|---|---|---|---|
| None | Normal Untreated Controls | 10 | — | 174.2 | — |
| Example 7- Table VI-A | Normal | 10 | 30*/I.P. | 836.0 | 4.78 |
| Example 7- Table VI-A | Normal | 10 | 30*/oral | 856.6 | 4.96 |
| None | Tx, 950R, BM Controls** | 10 | — | 73.6 | — |
| Example 7- Table VI-A | Tx, 950R, BM | 10 | 30*/I.P. | 740.4 | 10.10 |
| Example 7- Table VI-A | Tx, 950R, BM | 10 | 30*/oral | 474.0 | 6.42 |

*Similar results were obtained with 15 mg/kg. **Tx = Thymectomy.
R = Rads of total body irradiation
BM = Bone marrow reconstituted.

EXAMPLE 10

In a further set of experiments the effects of polymer from Example 7-Table VI-A on IgM antibody response to SRBC antigen (again using the Jerne Plaque assay method as in Example 9) were evaluated (1) in normal Lewis rats with polymer given either I.P. or orally and (2) in Lewis rats as a replacement for thymic function, again with polymer given either I.P. or orally. In case (1) the procedure followed that of Example 9. In case (2) normal thymic function was removed by adult thymectomy (Tx) which was surgically performed at the age of 8 to 12 weeks and high doses of total body irradiation (TBI) followed by bone marrow cell repopulation (BM). Thymectomy, total body irradiation and bone marrow cell repopulation were all done by standard procedures described by Falk, R. E. et al, *Surgery*, October (1978), by Falk, R. E. et al., *Abstract, Canadian Society for Clinical Investigation*, Jan. 24–27, 1978, Vancouver and by Falk, R. E. et al., *Abstract, Royal College of Physicians and Surgeons*, Jan. 25–28, 1978, Vancouver.

In these procedures TBI and BM repopulation were done the day following surgical thymectomy. For TBI the animals were irradiated using a $^{137}$cesium source (Atomic Energy of Canada). The dose of radiation in this machine is calibrated by the supplier and is applied in an equitable fashion over the entire body surface of animals placed in the container. For BM repopulation, single cell suspensions of bone marrow cells were prepared by washing the long bones of the femur and tibia in the rat with a balanced salt solution (BSS) at 4° C. The cells were washed three times in BSS and counted in a haemocytometer to determine viability and the appropriate cell dilution. Cells were administered I.V. using preparations with greater than 90% viability. To each rat BM repopulation involved $1 \times 10^8$ cells.

The mortality rate of animals for the total Tx+TBI+BM procedure was less than 10%. These animals were then allowed to recover for a period of 6 weeks prior to running the IgM antibody response to SRBC.

After the recovery period the polymer of Example 7-Table VI-A and the SRBC were administered as in Example 10. The results of the overall experiment are shown in Table VIII.

Various other examples as will further illustrate the invention can be carried out by substitution of other substantially equivalent materials for the specific materials recited in the foregoing examples.

Thus, propylene can be substituted for an equivalent amount of ethylene in the foregoing examples as illustrative of the defined olefin monomers with substantially similar results.

So also, citraconic anhydride can be substituted for an equivalent amount of maleic anhydride in the foregoing examples as illustrative of the defined polycarboxylic anhydrides with substantially similar results.

Polymers of still lower average molecular weight can be prepared by solvent-nonsolvent fractionation of the EMA polymer prepared in Example 1, above. This lower molecular weight polymer can then be substituted for an equivalent amount of the polymer of Example 1 in the foregoing examples with substantially similar results.

Other pharmaceutically acceptable salts of imides of the invention can be made by converting the ammonium salt derivatives to salts such as, for example, sodium and potassium. For example, the ammonium salt derivative of Example 3, Table IV, Run 4, above, can be converted to the half-amide, half free carboxyl derivative by passage of a 5% aqueous solution of the ammonium salt through a weak base cation exchange column, for example, Amberlite IRC-84 (crosslinked acrylic copolymer, Rohm and Haas Company). The resulting solution in the free carboxyl form can then be neutralized with either NaOH or KOH, respectively, and the neutralized solution freeze dried to obtain the corresponding sodium and potassium salt derivatives.

Detailed illustrative procedures for carrying out the foregoing further examples with the attendant results are as follows:

EXAMPLE 11

A low molecular weight copolymer of propylene and maleic anhydride was prepared in a similar manner as described in Example 1. To the reactor was charged 196 g. maleic anhydride dissolved in 1600 ml ethylbenzene containing 7.30 g benzoyl peroxide. The temperature was brought to 80° C. and the pressure adjusted to 40 psi by the addition of 42 g of propylene from a propylene cylinder mounted on a scale. Thereafter, propylene pressure was maintained at 40 psi over a period of 19 hours at the 80° C. reaction temperature. At the end of the run the bomb was cooled and vented and the slurry of propylene/maleic anhydride copolymer in ethyl benzene was worked up as described in Example 1 by three xylene slurry extractions followed by three hexane slurry extractions, filtration and drying with full oil pump vacuum at 60° C. The final product consisted of 269 g. and a 1.0 percent solution in DMF at 25° C. had a specific viscosity of 0.0590.

The low viscosity propylene/maleic anhydride copolymer (PMA) product prepared above was converted into the half primary amide-half ammonium carboxylate salt by the exact procedure described (for EMA) in Example 2a. From 26.0 g of PMA there was obtained 36.3 g of oven dried (35° C., 20–25 mm Hg vacuum) product. The functional composition by infra-red of the product indicated only the presence of primary amide, ionized carboxyl and ammonium carboxylate groups. No imide function was present.

The half amide-half ammonium carboxylate salt prepared from 0.059 specific viscosity PMA was converted into a partial imide containing composition by the procedure described in Example 3. A 20-gram sample of the amide-ammonium salt was slurried in 400 ml xylene and the slurry refluxed as in Example 3. The slurry was refluxed for 33 min. with the final temperature at 139° C. collecting 1.1 ml. water, and the product worked up as described obtaining 15.3 g. of final product. Infrared analysis of the product showed the 33 minute sample to contain 19.0 percent imide, in addition to amide and ammonium carboxylate functionality. The percent imide was determined in this case by referral to the standard imide/amide absorbency ratio-composition curve for EMA as described in Example 5. The pH of a 2% aqueous solution was 5.43 before adjustment and lyophilizing. After adjustment to pH 9.5, filtration and lyophilization the pH was 5.50, the % Nitrogen was 10.26 and the imide content was 19.0% by weight as determined by Infra-red.

The product was evaluated for its ability to stimulate immune responses in terms of increasing antibody producing cells to SRBC (antigen) stimulation as described in Example 9 with the following results:

|  | No. rats in group | PFC/1 × 10$^6$ Spleen Cells | Index Control = 1.0 |
| --- | --- | --- | --- |
| Controls | 4 | 587 | 1.00 |
| Test* | 4 | 793 | 1.35 |
| Controls | 2 | 468 | 1.00 |
| Test* | 2 | 614 | 1.31 |

*30 mg/Kg, I.P.

EXAMPLE 12

A low molecular weight copolymer of ethylene and citraconic anhydride was prepared in similar manner as described in Example 1. In this case the charge in reactor materials was 228.0 g citraconic anhydride in place of maleic anhydride, 1874 ml. ethyl benzene and 15.6 g benzoyl peroxide in 161 ml ethyl benzene. The ethylene pressure was maintained at 200 psi and the reaction was carried out at 70° C. for a total of 27½ hours. Further catalyst additions were made at 3 hr. and 20½ hr. consisting of 10.4 g benzoyl peroxide in 108 ml. ethyl benzene each. The ethylene/citraconic anhydride copolymer product, worked up as in Example 1 consisted of 73.5 g. The specific viscosity (1.0% in DMF, 25° C.) of the copolymer was 0.042.

The low viscosity ethylene/citraconic anhydride copolymer 29.5 g, 0.21 mole was converted to the half amide-half ammonium carboxylate salt by the procedure described in Example 2a with a recovery of 37.0 g vacuum dried product. Infra-red analysis indicated the presence of amide, ionized carboxyl and ammonium carboxylate functions but no imide functionality. A partial imide of the amide-ammonium carboxylate derivative was prepared using the procedure of Example 3 by refluxing a xylene (400 ml.) slurry of 20 g. of the above amide-salt for thirty minutes. The product yield was 15.7 grams and the I/A absorbency (infra-red) ratio was 1.21, which corresponds to 31.0% imide compared with the standard curve for EMA as described in Example 5. The percent nitrogen was 9.24% and a 5% solution in water had a pH of 5.31.

The product was evaluated as described in Example 9 for its ability to stimulate immune responses relative to increasing antibody producing cells to SRBC (antigen) stimulation with the following results:

|  | No. rats in group | PFC/1 × 10$^6$ Spleen cells | Index Control = 1.0 |
| --- | --- | --- | --- |
| Controls | 4 | 587 | 1.00 |
| Test* | 4 | 1259 | 2.14 |

*30 mg/Kg, I.P.

EXAMPLE 13

This example describes the preparation of a very low molecular weight EMA composition derived by solvent-non-solvent fractionation of EMA polymers described in Example 1. From eight separate EMA preparations there was amassed 1284 g EMA after drying overnight at 80° C. at full oil pump vacuum. These eight EMA products varied in specific viscosity (1%, DMF, 25° C.) from 0.051 to 0.058 (average 0.053) and their equivalent weights varied from 134 to 142 prior to solvent fractionation. Each of the eight runs (160 g) was dissolved in 500 ml. acetone and precipitated into 2.5 liters toluene during a 10 min. period in a 4-liter beaker vigorously stirred with a Lightnin ® Stirrer. The precipitated EMA was filtered (saving all eight primary mother liquor filtrates for soluble polymer work-up below) and the solids were slurried one time in 2 liters toluene and two times in 2 liters hexane, filtered and dried overnight at 50° C. at full oil pump vacuum. From the eight individual runs there was obtained a total of 1143 g of the solvent insoluble EMA which had an average specific viscosity of 0.057 (the eight solvent precipitated individual runs varied from 0.053–0.060 in specific viscosity).

The acetone-toluene soluble polymer fraction in the combined primary mother liquor filtrates above was concentrated to a heavy oil by evaporation of all solvents in a Rotavap on a boiling water bath at 25–30 mm Hg vacuum. The residue was dissolved in 200 ml acetone and precipitated into 1 liter toluene at room temperature to give an oily mushy solid. The supernate was decanted and the precipitate was redissolved in 200 ml acetone and reprecipitated into 1.2 liters xylene at 0° C. to give a solid white precipitate. This product was filtered, washed 2 times with 400 ml xylene and 2 times with 300 ml hexane and dried overnight at 50° C. at full oil pump vacuum. There was obtained 59 g of product which had a specific viscosity (1%, DMF, 25° C.) of 0.031, a calculated number average molecular weight of 342 and and equivalent weight by titration of 172.0. The percent carbon was 60.92, 60.61 and the percent hydrogen was 6.03, 6.12.

Five grams of the above 0.031 specific viscosity, 172 equivalent weight EMA fraction was converted to the half amide-half carboxyl ammonim salt by dissolving in 40 ml acetone and adding this solution to 200 ml acetone containing 5 ml liquid ammonia over a 20 minute period at −40° C. (dry ice bath). The slurry was stirred for one hour and then allowed to stand at room temperature overnight. The product was washed by slurrying in 80 ml acetone followed by three slurries in 80 ml hexane and obtaining 5.4 g of oven dried (50° C., pump vacuum) product. Five grams of this half amide-half carboxyl ammonium salt was converted to the partial imide by the procedure of Example 3 by refluxing in xylene for 1 hour. The final dry product (50° C, pump vacuum) consisted of 3.8 grams. This was dissolved in 70 g. water (pH-4.87) and adjusted to a pH of 9.4 with NH4OH, filtered through a 0.2 micron filter and dreeze dried. The final lyophilized product had a 2.0% aqeuous pH of 5.1, a total nitrogen content of 12.27 and an imide content of 25.0 wt. % (Product B).

An additional quantity of the half amide-half carboxyl ammonium salt of 0.031 specific viscosity EMA was prepared by dissolving 10 grams of EMA (0.031 sp. visc.) in 40 ml acetone, filtering the acetone solution, and adding the solution over a period of 13 minutes to 170 ml acetone, pre-saturated with ammonia gas and with gaseous ammonia bubbling through the reaction mixture during the 13 min. addition period. First addition was made at 21° C. and the reaction mixture temperature rose to 37.0° C. during the EMA addition. The final slurry was filtered and the product AEMA (from 0.03 sp. visc. EMA) washed with 70 ml acetone on the filter. The product was reslurried twice in 150 ml acetone and twice in 150 ml hexane, filtered and dryed at 50° C., pump vacuum to give 10.1 g. of AEMA. This was dissolved in water (pH 4.58), adjusted to a pH of 8.5 with NH4OH, filtered through a 0.2 micron filter and freeze dried. The final lyophilized product had a 2.0% aqueous pH of 6.58 (Product A).

For further comparison of preparative methodology a sample of EMA of 0.06 specific viscosity was converted to the ammoniated derivative (AEMA) by the procedure described for Product A above (Example 13) yielding Product C having a 2.0% aqueous pH of 6.20 and a nitrogen content of 13.96%.

Infra-red analysis of Product A (AEMA from 0.03 sp. visc. EMA) and Product C (AEMA from 0.06 sp. visc. EMA) showed no detectable imide content at 1720 $cm^{-1}$; only primary amide at 1670 $cm^{-1}$ and 1620 $cm^{-1}$ and carboxylate ion at 1560–1570 $cm^{-1}$ and ammonium carboxylate at 1405–1400 $cm^{-1}$. However, the ratio of the carboxylate absorbency to primary amide absorbency was increased (not quantified) over that shown by AEMA prepared by the procedure described in Example 2(a).

Products A, B and C were evaluated for their ability to stimulate immune responses in terms of increasing IgM antibody producing cells to sheep red blood cell (antigen) stimulation as described in Example 9 with the following results:

| Product A, Example 13 (AEMA from 0.03 sp. visc. EMA) | | | |
|---|---|---|---|
| | No. rats in group | IgM-PFC/ $1 \times 10^6$ Spleen cells | Index Control = 1.0 |
| Controls | 9 | 946 | 1.00 |
| Test* | 3 | 691 | 0.73 |
| Test* | 5 | 907 | 0.96 |
| Controls | 3 | 1003 | 1.00 |
| Test* | 3 | 691 | 0.69 |
| Controls | 2 | 1000 | 1.00 |
| Test* | 3 | 832 | 0.83 |
| Controls | 2 | 996 | 1.00 |
| Test* | 2 | 1020 | 1.02 |

*30 mg/Kg, I.P.

| Product B, Example 13 (partial imide from 0.03 sp. visc. EMA) | | | |
|---|---|---|---|
| | No. rats in group | IgM-PFC/ $1 \times 10^6$ Spleen cells | Index Control = 1.0 |
| Controls | 10 | 562 | 1.00 |
| Test* | 7 | 1131 | 2.10 |
| Test** | 4 | 840 | 1.49 |
| Controls | 2 | 709 | 1.00 |
| Test* | 4 | 1173 | 1.65 |
| Controls | 7 | 523 | 1.00 |
| Test* | 4 | 1232 | 2.35 |

*30 mg/Kg, I.P.
**30 mg/Kg, Orally

| Product C, Example 13 (AEMA from 0.06 sp. visc. EMA) | | | |
|---|---|---|---|
| | No. rats in group | IgM-PFC/ $1 \times 10^6$ Spleen cells | Index Control = 1.0 |
| Controls | 9 | 946 | 1.00 |
| Test* | 5 | 712 | 0.75 |
| Controls | 3 | 779 | 1.00 |
| Test* | 3 | 709 | 0.91 |
| Controls | 2 | 758 | 1.00 |
| Test* | 2 | 720 | 0.95 |

*30 mg/Kg, I.P.

EXAMPLE 14

The preparation and utility of sodium and potassium salts of imides of the invention were demonstrated as follows. The ammonium salt derivatives was prepared by methods described in Examples 1, 2a and 3-IV-5 and had the following analyses on the freeze dried product:

| Total % Nitrogen | 14.15, 13.99 |
|---|---|
| % Nitrogen in $NH_4^+$ | 6.16, 6.09 |
| pH - 2% aqueous | 6.28 |
| Wt. % Imide by I.R. | 20.5 |
| Meq. $NH_4^+$/g. by $NH_3$ electrode | 4.31 |

The corresponding sodium and potassium salts of the above imide of the invention were prepared by conventional ion exchange techniques using Rohm and Haas IRC-120 in either the sodium form or potassium form. These columns were prepared by loading 400 ml. of IRC-120 ($H^+$form) into an appropriate column and generating the $Na^+$resin by treatment with 3.8 liters of 1.0 molar NaCl (or 1.0 molar KCl in the case of potassium) followed by 4 liters of water. Solutions of the above $NH_4^+$salt of the imide containing polymer were prepared using 5.0 g of polymer dissolved in 200 ml of water. These solutions were then adjusted to a pH of 8.0 with dilute NaOH (or KOH in the case of potassium). These pH adjusted solutions were passed through the respective Na or K columns at a flow rate of 15 ml/min. followed by water until 500 ml of effluent was collected in each case. These effluents were adjusted to 6.8-7.0 with HCl and freeze dried. The final freeze dried salts had the following properties:

| Salt Form: | $NH_4^+$ | $Na^+$ | $K^+$ |
|---|---|---|---|
| Yield, g.* | — | 5.47 | 5.80 |
| Nitrogen % total | 14.07 | 7.77 | 7.00 |
| meq. $NH_4^+$/g. | 4.31 | 0.034 | 0.036 |
| $NH_4^+$ converted to salt, % | — | 99.3 | 99.3 |
| Chlorine, % | — | 1.25 | 1.22 |
| Na or K, % | — | 10.45 | 17.08 |

*from 5.00 g $NH_4^+$ salt, contains NaCl or KCl from pH adjustment with HCl

The above salts were evaluated for their ability to stimulate immune responses in terms of increasing IgM antibody producing cells to heterologous erythrocytes (SRBC) as described in Example 9 with the following results:

| Polymer Source Salt Type- | No. Rats in Group | IgM-PFC/ $1 \times 10^6$ Spleen Cells | Index Control = 1.0 |
|---|---|---|---|
| Control | 2 | 500 | 1.00 |
| Ammonium ($NH_4^+$) | 4 | 1052 | 2.10 |
| Control | 4 | 534 | 1.00 |
| Sodium ($Na^+$)* | 4 | 970 | 1.82 |
| Potassium ($K^+$)* | 4 | 1098 | 2.06 |
| Control | 2 | 538 | 1.00 |
| Sodium ($Na^+$)* | 2 | 1373 | 2.55 |
| Potassium ($K^+$)* | 2 | 996 | 1.85 |
| Sodium ($Na^+$)** | 3 | 1523 | 2.83 |
| Potassium ($K^+$)** | 3 | 1058 | 1.97 |
| Control | 6 | 541 | 1.00 |
| Sodium ($Na^+$)* | 5 | 1254 | 2.32 |
| Potassium ($K^+$)* | 5 | 1044 | 1.93 |
| Sodium ($Na^+$)** | 6 | 1607 | 2.97 |
| Potassium ($K^+$)** | 6 | 1003 | 1.85 |

*30 mg./Kg. given I.P.
**30 mg./Kg. given orally.

EXAMPLE 15

This example utilizes the procedure described in Example 9 to evaluate normal Lewis rats for their ability to stimulate immune responses in terms of increasing IgM antibody producing cells to heterologous erythrocytes (sheep red blood cells, SRBC) except in this case the imide composition of the invention was administered by intravenous dosage via the tail vein as 1 ml. of physiological saline containing the indicated dosage amount. All other details were the same as in Example 9. The following data were obtained in two experiments.

| | Polymer from Example 7-VI-A | | Polymer from Example 3-IV-5 | |
|---|---|---|---|---|
| Intravenous Dosage mg/Kg. | IgM PFC/1 × $10^6$ Spleen Cells | Stimulation Index Control = 1 | IgM PFC/1 × $10^6$ Spleen Cells | Stimulation Index Control = 1 |
| 0 (control) | 562* | 1.00 | 522** | 1.00 |
| 32 | 1298 | 2.31 | 1406 | 2.69 |
| 16 | 1138 | 2.02 | 1282 | 2.46 |
| 8 | 1215 | 2.16 | 1684 | 3.23 |
| 4 | 1178 | 2.10 | 1882 | 3.61 |
| 2 | 1144 | 2.04 | 1238 | 2.37 |
| 1 | 1257 | 2.24 | 1100 | 2.11 |
| 0.5 | 1173 | 2.09 | 1844 | 3.53 |
| 0.1 | 1021 | 1.87 | 1022 | 1.96 |

*5 Animals per group
**2 animals per group

What is claimed is:

1. The method of regulating an immune response in a warm-blooded animal suffering from an immune reaction comprising administering to said animal an effective immune regulatory amount of a composition selected from the group consisting of a copolymer of at least one olefin monomer having from 2 to about 4 carbon atoms and at least one $\alpha,\beta$-unsaturated polycarboxylic anhydride having from 4 to about 6 carbon atoms, having an average molecular weight of from about 300 to about 1500, and derivatized to contain both (a) half-amide, half-carboxyl acid groups and (b) imide groups in which said imide groups comprise from about 5% by weight to about 40% by weight of said derivatized groups, and the pharmaceutically acceptable cationic salt derivatives of said derivatized copolymer.

2. The method of claim 1 in which the composition is administered in an amount of from about 0.1 to about 100 mg/kg of body weight of said animal.

3. The method of claim 1 in which the copolymer is a copolymer of ethylene and maleic anhydride.

4. The method of claim 3 in which the (a) half-amide, half-carboxyl acid group is derivatized to the half-amide, half-ammonium salt.

5. The method of claim 3 in which the (b) imide group comprises from about 10% to about 25% of said derivatized groups.

6. The method of claim 3 in which the copolymer has an average molecular weight of about 850.

7. The method of claim 3 in which the (a) half-amide, half-carboxyl acid group is derivatized to the half-amide, half-ammonium salt, the (b) imide group comprises about 20% by weight of said derivatized groups, and in which the copolymer has an average molecular weight of about 850.

* * * * *